United States Patent
Klebanoff et al.

[11] 4,002,996
[45] Jan. 11, 1977

[54] LEVEL DETECTOR USING OSCILLATOR CIRCUIT WITH TWO CAPACITIVE PROBES

[75] Inventors: Leonard Klebanoff, Willowdale; Donald Binnee, Richmond Hill, both of Canada

[73] Assignee: Elkay Electronics Ltd., Agincourt, Canada

[22] Filed: June 18, 1975

[21] Appl. No.: 587,989

[52] U.S. Cl. .............................. 331/65; 73/304 C; 128/214 E; 137/392; 324/61 P; 331/108 B; 340/244 C

[51] Int. Cl.² .................. A61M 5/14; G01F 23/26; H03B 5/12

[58] Field of Search ................ 331/65, 108 B, 110, 331/135; 340/244 R, 244 C; 73/290 R, 304 C; 324/61 R, 61 P; 128/214 E; 137/392

[56] References Cited
UNITED STATES PATENTS

| | | | |
|---|---|---|---|
| 3,042,908 | 7/1962 | Pearson | 331/65 X |
| 3,254,333 | 5/1966 | Baumoel | 73/304 C X |
| 3,588,859 | 6/1971 | Petree | 340/244 R |

*Primary Examiner*—Siegfried H. Grimm
*Attorney, Agent, or Firm*—Fetherstonhaugh & Co.

[57] ABSTRACT

This invention relates to a device for detecting a fall of level of flowable material in a closed container by emitting an oscillation. It is electronic in nature and the circuit has an amplifier with a feed-back terminal that is connected to a feed-back network. The feed-back network in turn includes two vertically spaced apart identical probe condensers each having an open dielectric space and each being in different feed-back paths of the feed-back network. The feed-back network is activated as the level of the flowable material drops, whereby the difference in the dielectric material of the condensers provides a change in input current to the amplifier. The circuit is responsive to a positive change in input current to cause the amplifier to commence oscillation on dropping of the level past the condensers to signal the drop of the level of the flowable material. The device is stable in design, low in cost and easy and reliable to use. In particular it requires no adjustment with variations of flowable material.

7 Claims, 4 Drawing Figures

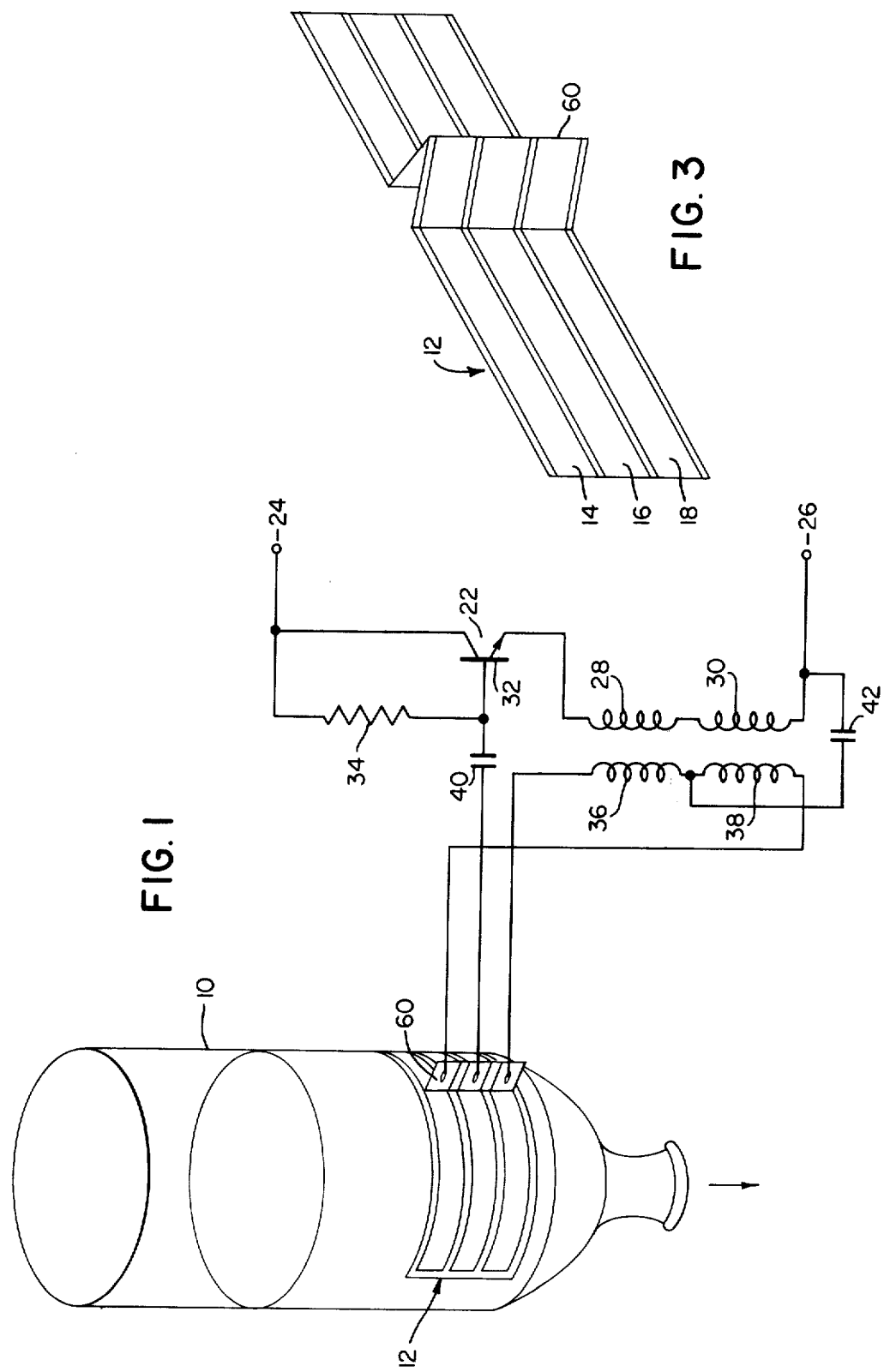

LEVEL DETECTOR USING OSCILLATOR CIRCUIT WITH TWO CAPACITIVE PROBES

This invention relates to a device for electronically detecting the level of a flowable material within a container. It employs a capacitor probe technique and a principal application is the detection of a predetermined low level limit of an intravenous solution within its container. It will be described in connection with such an application, but its application is broader and could be used to determine a level of any flowable material, liquid or granular or gaseous, capable of occupying the open dielectric space of the capacitive probes.

It is an object of the invention to provide a device for detecting levels that is stable in design, low in cost and easy and reliable to use.

With these and other objects in view, a device for detecting a predetermined level of a flowable material by the emmission of an oscillation according to this invention comprises a circuit, said circuit having an amplifier with a feed-back terminal, a feed-back network including two vertically spaced apart probe condensers each having an open dielectric space, said probe condensors each being in different feed-back paths of said feed-back network, said probe condensers each having a similar plate configuration and said feed-back paths being similar whereby the magnitude of current through each of said condenser is subtantially the same when the open dielectric space of said two probe condensers is filled with the same dielectric material and is substantially different when the dielectric space of one probe condenser is filled with different dielectric material to the dielectric space of the other probe condenser, means for deriving a resultant feed-back signal from the difference between the magnitudes of the currents through said probe condensers, the current through the upper condenser contributing a negative feed-back component to said resultant feed-back signal and the current through the lower condenser contributing a positive component to said resultant feed-back signal, said circuit being responsive to a positive resultant feed-back signal to said feed-back terminal to oscillate.

The invention will be clearly understood after reference to the following detailed specification read in conjunction with the drawings.

In the drawings:

FIG. 1 is a schematic illustration of a bottle containing an intravenous solution that is being fed to a patient through the downwardly extending opening and the circuit elements of a solution level indicating device;

FIG. 3 is an illustration of a probe condenser assembly; and

Figure 4:
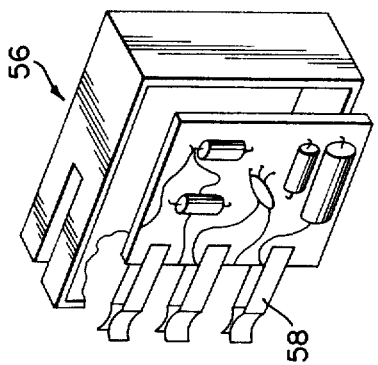
FIG. 4 is an illustration of a physical embodiment of circuitry used for the invention.

Referring to the drawings, FIG. 1 is an illustration of an intravenous feeding bottle 10 with a probe condenser plate assembly generally indicated by the numeral 12 adhesively secured thereto and circuitry for detecting the drop of the liquid to a level slightly below the level of the plate structure of the upper condenser of the condenser plate assembly. It is important in the use of intravenous feeding techniques to have an alarm when the level of the liquid drops below a certain level because of the danger of admitting air to the vein system of the patient. This invention is capable of detecting the drop of the liquid level in the bottle 10.

The condenser plate assembly generally indicated by the numeral 12 comprises a web of non-conducting tape with an adhesive on its back face so that it can be adhesively secured to the bottle 10 as shown and three strips of metallic foil 14, 16 and 18 mounted on its front face to form a physically similar plate structure for two condensers. It will be noted that each of the strips 14, 16 and 18 are of the same size and that they are equally spaced apart so that a condenser formed by the plates 14 and 16 is of the same value as a condenser formed by the plates 16 and 18 provided that the dielectric material in the open dielectric space between the plates of the said two condensers is the same. The dielectric material for the condensers is the matter between their respective plates and in each case includes the glass of the bottle and a substance on the inside of the bottle, be it air or liquid. It will be apparent that the presence or absence of liquid on the inside of the bottle at the plate or strip level will materially effect the value of the condensers and it is this change in condenser value due to change of liquid level that triggers the signal of the drop in liquid level. The broad principle of detecting a drop in liquid level by change of dielectric of a condenser due to level drop is not new and no claim is made to it. This invention is concerned with a method and circuit for detecting the liquid drop.

The level detecting circuit has a transistor 22 connected across a 9 volt D.C. voltage supply 24 and 26 through low impedance coils 28 and 30. The base 32 of transistor 22 is biased through resistor 34 so that in use transistor 22 is normally conducting.

Coil 36 is inductively coupled to coil 28 and coil 38 is inductively coupled to coil 30. One end of coil 36 connects with base 32 of transistor 22 through the condenser whose plates are formed by the strips 16 and 18 and one end of coil 38 connects with the base 32 of transistor 22 through a condenser whose plates are formed by the strips 16 and 14. Thus, from the point between coils 36 and 38 there are two current paths to the base 32 of the transistor 22. Coil 28 is identical to coil 30, coil 36 is identical to coil 38 so that subject to the capacitance of the two condensers formed by the strips 14, 16 and 18 being identical, the feed-back paths from the output of the transistor 22 to the base 32 thereof are of equal impedance. It will be noted, however, that by reason of the interconnection, the polarity of any feed-back from the output of transistor 22 to the base 32 thereof through the separate feed-back paths will be reversed, i.e. the feed-back through one path will be 180° out of phase with the feed-back through the other. Thus, under conditions of operation where the condensers formed by the strips 14, 16 and 18 are the same in value, the feed-back signals to the base through the coils will be equal and of opposite phase. Under these conditions, the resultant feed-back voltage applied to the base is zero and the transistor 22 does not oscillate.

If, however, the dielectric occupying the space between the plate structure consisting of strips 14 and 16 should change from liquid to air as a result of the drop of level in the bottle while the dielectric occupying the space of the condenser comprised by plates 16 and 18 should remain as liquid, the negative component of feed-back signal to the base 32 would be reduced with respect to the positive component of feed-back signal and the circuit oscillates.

It has been found that the feed-back path can be designed such that the reduction in negative feed-back signal caused by the change in dielectric from liquid to air in the case of the upper condenser, the lower condenser, remaining liquid, is sufficient to cause oscillation of the amplifier transistor 22. The oscillation of the circuit is detected by a detector (not shown) of any suitable design to signal the drop of the liquid level in the container to just below the level of the dielectric between the top condenser.

As the liquid level in the container drops further and below the level of the bottom condenser, the plates of which are formed by the strips 16 and 18, the dielectric for the two condensers again becomes the same. When this occurs, the impedance of the two feed-back paths to the base 32 of the transistor 22 is the same and the positive feed-back signal and the negative feed-back signal are again equal. The circuit ceases to oscillate and commences to conduct D.C. as before.

Since the circuit works on the principle of detecting the imbalance in the positive and negative feed-back paths through the liquid, it is essentially insensitive to the dielectric properties of the liquid being monitored. Also, the static balance of the circuit, i.e. balancing the positive and negative feed-back paths so that no oscillation occurs, is automatically achieved if the mechanical dimensions of the conducting strips on the sensing tape are the same and the solution being sensed is electrically homogeneous.

In order for oscillation to take place, the negative (stabilizing) component of the feed-back must be reduced first leaving the positive component to generate the oscillations. If the liquid level moved in such a manner that the positive component was reduced first, the negative component would dominate and the circuit would not oscillate. Thus, the circuit will only operate for the liquid level changing in the direction that will reduce the negative feed-back component first. The sensor could be used to monitor when a liquid reaches a predetermined height as the liquid reaches the positive feed-back path first, the positive feed-back is increased and causes the circuit to oscillate. In the case of detecting rising liquids, one increases the positive feed-back first while in the case of detecting dropping liquid level, one decreases the negative feed-back first. The net result is the same, i.e. the resultant goes positive and the circuit oscillates.

The capacitors 40 and 42 provide isolation from possible A.C. supply current leakage through the sensor tape to the patient. This eliminates any potential shock hazard to a patient with use of the invention for intravenous feeding. Condenser 42 also provides a low impedance R.F. path to ground for the common point of coils 36 and 38.

Coil 36 is preferably inductively coupled to coil 28 by winding coil 28 over coil 36. Similarly, coil 30 is inductively coupled to coil 38. Thus, voltages are induced in coils 36 and 38 simultaneously as indicated above. Coil 36 feeds current back to the base of transistor 22 through the capacitance between the lower strip and the centre sensing strip. The coil is so wound that this current is in a positive sense and the circuit will oscillate if it were not for the effect of current fed back to the base of transistor 22 through the capacitance formed by the centre strip and the upper strip. This current is, because of the choice of connection of coil 30, in the negative sense and essentially cancels out the positive current through coil 36 to prevent oscillation when the two condensers have identical dielectric material as noted above.

The circuit oscillates because of the design of the feed-back paths. The frequency of oscillation is not important, but it does depend on the values of the inductors and dielectric characteristics of the liquid that comprise the oscillating feed-back circuit.

Important advantages of this circuit as a liquid sensor is that is low in cost, has a small component count and provides extremely high sensitivity. The circuit has only a single "on state" and a single "off state" so that the signal-to-noise ratio is essentially infinite. The sensitivity is high because only a small amount of positive feed-back signal is required to enable the circuit to oscillate. High sensitivity can be obtained without the use of a number of cascaded high-gain amplifier stages.

It has been found that there is a sufficient difference in dielectric value between any liquid tested and air to trigger the circuit upon the dropping of the liquid level. It is contemplated that the device could also be used to indicate levels of granular materials such as grain.

Figure 2:
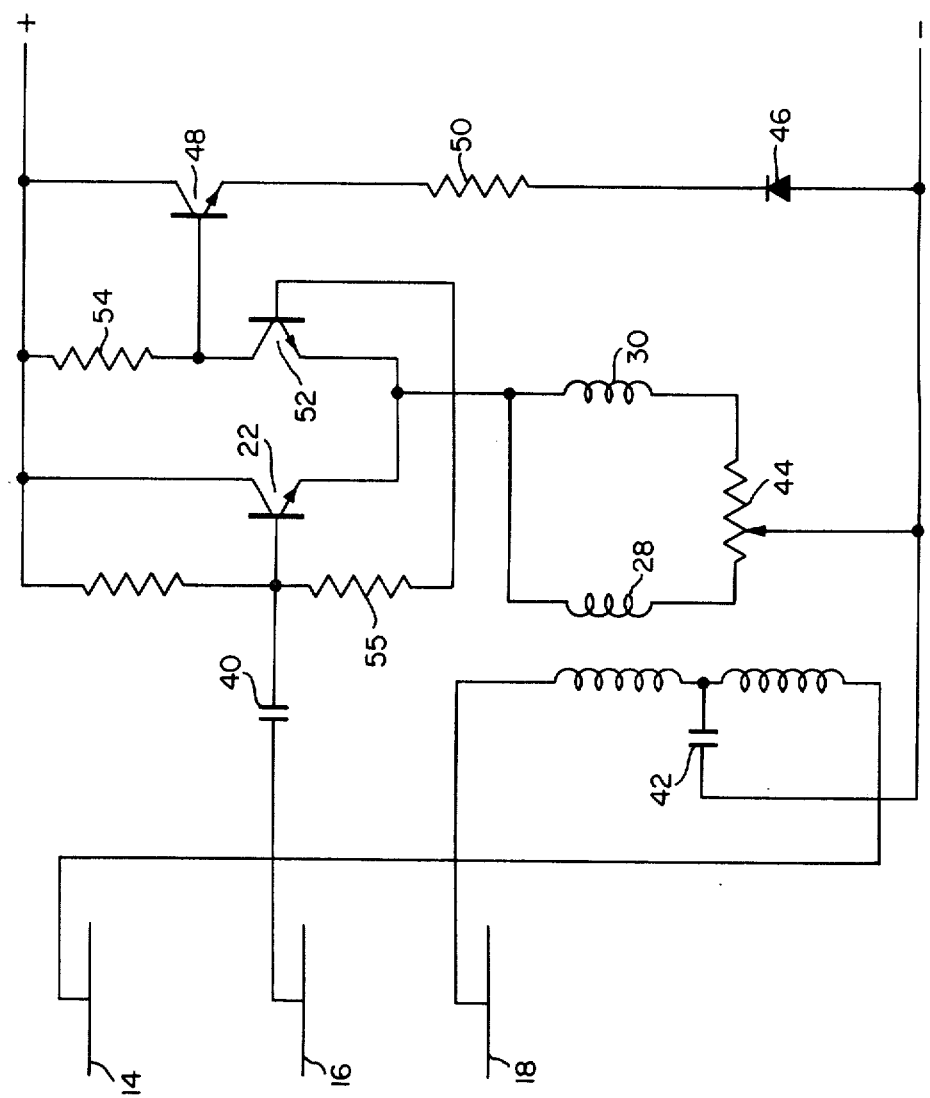
FIG. 2 is an illustration of a modified circuit of the level indicating device together with the circuit elements of an alarm circuit.

FIG. 2 is a sketch of the circuit with modifications. It may be desirable to connect coils 28 and 30 in parallel and use a potentiometer generally indicated by the numeral 44 to adjust the balance of the negative and positive feed-back signals so that the circuit elements in the two feed-back paths are the same.

The alarm that responds to the conditions of oscillation of transistor 22 can take many forms. In FIG. 2, circuitry for operating two alarm devices is indicated. Numeral 48 refers to an amplifier that is series connected with a resistor 50 and a light emitting diode 46. The base of transistor 48 is biased by resistor 54, but under conditions of non-oscillation of transistor 22, there is not sufficient bias on the base of transistor 48 to render it conducting. In this connection, transistor 52 which is biased through its bias resistor 54 conducts electricity under conditions of non-oscillation of the transistor 22 through resistor 54 and low impedance windings 28 and 30. The impedance of coils 28 and 30 under these conditions of flow is so small that there is essentially no voltage on the base of transistor 48 and it does not conduct.

When the transistor 22 goes into a condition of oscillation, the D.C. voltage on the base of transistor 22 goes negative and transistor 52 ceases to conduct electricity. When this occurs, the bias on the base of amplifier 48 is increased and it begins to conduct. As it conducts, it lights the light emitting diode 46 to give an alarm signal and a voltage appears across the resistor 50.

The voltage across resistor 50 and the light emitting diode is used to operate a further alarm that has a time delay after the occurrence of the voltage. The time delay is used to eliminate false alarms due to the affect of the liquid moving within the container as a result of a jolt or testing of the equipment. The second alarm is preferably located at a remote nursing station in the case of an intravenous feeding device.

The alarm 46 is almost instantaneous in operation and it can be used to test the circuit. One can put transistor 22 into oscillation by passing one's finger across the metallic strips that form the plates of the capacitors in the feed-back circuits. This action will sufficiently change the balance of the circuits to trigger the oscillation and cause the signal light 46 to glow. At the same time, it is not desirable to have the signal at the nurses' station respond to this instantaneous tripping of the alarm system and as indicated the signal at the remote station preferably has a 10 second time delay. In the event that the oscillator is operated by the falling of the liquid level, the alarm 46 would operate immediately and, within ten seconds, the alarm at the remote station would operate as a result of the voltage across resistance 50. Resistance 55 is a bias resistor for transistor 52.

Thus, in order to test the operability of the oscillating circuit, one has merely to physically run the hand over the tapes 14 and 16 to trigger the oscillator and light the diode 46.

The particular design is especially suited to a test alarm which can be used to determine the operability of the device without operating the principal alarm that is subject to a reasonable delay.

The electronics of the device as illustrated in FIGS. 1 and 2 can be incorporated into a small casing generally indicated by the numeral 56 and having spring loaded connectors 58 designed to slip over a tab 60 formed by making folds in the strip 12 that carries the metallic strips 14, 16 and 18. As indicated, the back face of strip 12 carries an adhesive for its adhesive securement to the bottle and the folding of the strip to form a connecting tab that co-operates with the slide-on type connectors 28 is an extremely positive and simple way to make the interconnection of the circuit with the capacitor plates that are mounted on the bottle.

Uses other than the one indicated will be apparent to those skilled in the art and it is intended that the device could be used for the determination of levels of materials other than liquids, for example, it could be used to detect the difference in level of a granular material, the only requirement is that the material flow occupy the free space between the condenser plates.

Moreover, it will be apparent that the form of the condenser plates could change. It is only necessary that the condenser plate construction of the two condensers be the same so that the capacitance of the two condensers will be equal when they are occupied by the same dielectic material. It would, for example, be possible to have separately formed condensers spaced a substantial distance apart. It would also be possible to have a condenser formed from stips, the outer two of which were either larger or smaller than the middle one. The only requirement is that the plate structure of the two condensers be the same and that the spacing of the plates be the same.

Embodiments of the invention other than the one illustrated will be apparent to those skilled in the art.

In the embodiment illustrated, the two feed-back paths have probe condensers with identical plate structures and identical fixed components. The paths are connected so that the components of feed-back signal from each of them are 180° out of phase. Thus, as explained, when the dielectric space of both probe condensers if filled with the same dielectric material, the components of signal voltage derived from each of the feed-back paths is the same in magnitude, but different in phase. They, therefore, cancel each other out. By changing the dielectric in the open dielectric space in use, one reduces the size of the negative component whereby to cause the resultant to become more positive to oscillate the circuit. This occurs in the circuit illustrated as the liquid level drops to just below the open dielectric space of the first probe condensor. The condition remains as long as the first probe condenser has air in its open dielectic space and the second probe condenser has liquid in its open dielectric space. When the liquid level drops below the second probe condenser, both condensers again have air in their open dielectric space and the feed-back signals are again equal and cancel out. Oscillation stops. The opposite occurs with rising liquid in a bottle. If the bottle were to be filled from the bottom to cause the liquid level to rise, the liquid level would first fill the open space between the condenser plates of the lower probe electrode. This would cause the resultant feed-back signal to go positive and to oscillate the circuit. As the liquid level rises still further to fill the upper condenser, both probe condensers have similar dielectric material in their open dielectric space and the resultant feed-back signal drops to zero and there is no oscillation.

Embodiments of the invention other than the one illustrated will be apparent to those skilled in the art.

The probe condensers in their different feed-back paths of the feed-back network have a similar plate configuration and the feed-back paths are similar so that the magnitude of the current through each of the condensers is substantially the same when the open dielectric space of the probe condensers is filled with the same dielectric material and is substantially different when the dielectric space of one probe condenser is filled with a different dielectric material to the dielectric space of the other probe condenser.

In the embodiment of the invention illustrated, the feed-back path that goes through each of the probe condensers is common for a portion of its extent from the emitter of the transistor 22 and the means for deriving the resultant feed-back signal from the difference between the magnitudes of the current through the condensers, i.e. the phase shifting connection of the windings 36 and 38, is in advance of the probe condensers in the feed-back network.

It would be equally possible to locate the means for deriving the resultant feed-back signal that determines the difference between the magnitude of the currents through the probe condensers by locating the phase shifting device in the feed-back paths between the probe condensers and the feed-back terminal of the transistor 22. For example, one could arrange the feed-back network such that the currents through the probe condensers were the same in phase and applying the signal from one probe condenser to one terminal of a differential amplifier and the signal from the other probe capacitor to the other terminal of a differential amplifier. The output of the differential amplifier would be a resultant that would have a phase depending upon the magnitude of the inputs. The condensers would be connected to the differential amplifier so that the current through the upper condenser contributed a negative feed-back component to the resultant and the feed-back through the lower condenser contributed a positive component to the resultant feed-back signal.

The embodiments of the invention in which an exclusive property or privilege is claimed are defined as follows:

1. A device for detecting a predetermined level of flowable material in a closed container by emitting an oscillation comprising a circuit, said circuit having an amplifier with a feed-back terminal, a feed-back network including two vertically spaced apart probe condensers each having an open dielectric space, means for connecting said feedback terminal to said feed-back network, said probe condensers each being in different feed-back paths of said feed-back network, said probe condensers each having a similar plate configuration and said feed-back paths being similar whereby the magnitude of the current through each of said condensers is substantially the same when the open dielectric space of said two probe condensers is filled with the same dielectric material and is substantially different when the dielectric space of one probe condenser is filled with different dielectric material to the dielectric space of the other probe condenser, means for deriving a resultant feed-back signal from the difference between the magnitudes of the currents through said probe condensers, the current through the upper condenser contributing a negative feed-back component to said resultant feed-back signal and the current through the lower condenser contributing a positive component to said resultant feed-back signal, said circuit being responsive to a positive resultant feed-back signal to said feed-back terminal to oscillate.

2. A device for detecting a predetermined level of flowable material in a closed container by emitting an oscillation as claimed in claim 1 in which said means for deriving a resultant feed-back signal comprises means for supplying said probe condensers with a feed-back current of opposite phase.

3. A device for detecting a predetermined level of flowable material in a closed container by emitting an oscillation as claimed in claim 1 in which the different feed-back paths contain similar circuit elements.

4. A device for detecting a predetermined level of flowable material in a closed container by emitting an oscillation as claimed in claim 1 in which the plate structures of said probe condensers are formed by a series of three parallel spaced strips of metallic foil carried by a web of non-conducting material, said web being mountable on the outer wall of a container for a flowable material with said strips in parallel relation to the level in the container.

5. A device for detecting a predetermined level of flowable material in a closed container by emitting an oscillation as claimed in claim 1 having an alarm circuit that includes an alarm amplifier series connected with at least one alarm device, said alarm amplifier having a base normally biased to maintain said alarm amplifier nonconducting, and means for applying bias to said base of said alarm amplifier to render said alarm amplifier conducting and operate said alarm device upon oscillation of said feed-back amplifier.

6. A device for detecting a predetermined level of flowable material in a closed container by emitting an oscillation as claimed in claim 3, in which the plate structures of said probe condensers are formed by a series of three parallel spaced strips of metallic foil carried by a web of non-conducting material, said web being mountable on the outer wall of a container for a flowable material with said strips in parallel relation to the level in the container.

7. A device for detecting a predetermined level of flowable material in a closed container by emitting an oscillation as claimed in claim 3 having an alarm circuit that includes an alarm amplifier series connected with at least one alarm device, said alarm amplifier having a base normally biased to maintain said alarm amplifier non-conducting, and means for applying bias to said base of said alarm amplifier to render said alarm amplifier conducting and operate said alarm device upon oscillation of said feed-back amplifier.

* * * * *